United States Patent [19]

Narabayashi

[11] Patent Number: 4,562,584
[45] Date of Patent: Dec. 31, 1985

[54] APPARATUS FOR MEASURING VOID RATIOS BY USING RADIATION

[75] Inventor: Tadashi Narabayashi, Ichikawa, Japan

[73] Assignee: Tokyo Shibaura Denki Kabushiki Kaisha, Kanagawa, Japan

[21] Appl. No.: 446,052

[22] Filed: Dec. 1, 1982

[51] Int. Cl.⁴ .............................................. G01B 15/02
[52] U.S. Cl. ........................................ 378/54; 378/146
[58] Field of Search ..................... 378/54, 146, 55, 56

[56] References Cited

U.S. PATENT DOCUMENTS 3,796,874  3/1974  Roller ..................................... 378/54
4,260,898  4/1981  Annis ..................................... 378/146
4,282,433  8/1981  Loffel .................................... 378/54
4,342,914  8/1982  Bjorkholm ........................... 378/146

Primary Examiner—Craig E. Church
Attorney, Agent, or Firm—Stevens, Davis, Miller & Mosher

[57] ABSTRACT

In apparatus for measuring a void ratio by using radiation of the type comprising a hollow measuring unit through which fluid containing voids flows, a source of radiation and a radiation detector which are disposed on the opposite sides of the measuring unit, there is provided a rotary disc disposed between the measuring unit and the radiation detector and provided with a plurality of measuring openings which are equally spaced around a periphery of the rotary disc for transmitting the radiation.

2 Claims, 7 Drawing Figures

APPARATUS FOR MEASURING VOID RATIOS BY USING RADIATION

BACKGROUND OF THE INVENTION

This invention relates to apparatus for measuring the ratio between gas and liquid in pipes of a nuclear reactor or a boiler through which high temperature and high pressure steam and water flow.

A mixed fluid consisting of a vapor phase fluid as steam and a liquid phase fluid as water is generally termed a two phase fluid, and the ratio of the steam in the two phase fluid is called a void ratio. The void ratio is one of the important items of measurement in a nuclear reactor and a boiler in which a two phase fluid exists.

FIG. 1 shows a prior art void ratio measuring apparatus utilizing radiation. More particularly, a source of X rays 2 and a X ray detector 3 are disposed on the opposite sides of a cylindrical measuring unit 1, and X rays 4 are collimated into parallel beams by a collimeter 5. Then, the X rays transmit through the cylindrical measuring unit 1 to enter into the X ray detector 3 through slits or small openings 6. The output signal from the X ray detector 3 is sent to a signal processing circuit, not shown, via a cable 7. Bubbles of steam entrained in a liquid flowing through the cylindrical measuring unit 1 are designated by reference numerals 8.

In the prior art void ratio measuring apparatus described above, let us denote the output voltages of the detector 3 when the measuring unit 1 is empty and filled with water by $I_A$ volt and $I_W$ volt respectively, and the output voltage of the detector 3 when the two phase fluid to be measured is flowing through the measuring unit 1 by $I_X$ volt. Then the void ratio $\alpha$ is given by the following equation.

$$\alpha = \frac{\rho_W}{\rho_W' - \rho_V'} \cdot \frac{\log(I_X/I_W)}{\log(I_A/I_W)} - \frac{\rho_W - \rho_W'}{\rho_W' - \rho_V'}$$

where $\rho_W$ represents the density of water at normal temperature, $\rho_W'$ that of high temperature water and $\rho_V'$ the density of steam.

The void ratio $\alpha$ can be equivalently expressed by an equation $$\alpha = \left[ \sum_{i=1}^{n} l_i \right] / l_D$$

where $l_i$ represents the length of X ray beam 4 transmitting through one of the steam bubbles 8 prevailing in the cylindrical measuring unit 1 (where a plurality of bubbles present the length are shown by $l_1, l_2, \ldots l_i \ldots l_n$), and $l_D$ the lengths of the X ray beams 4 transmitting through the measuring unit 1.

Thus, the void ratio measured by the X ray void ratio measuring apparatus is defined by a ratio of the length $l_D$ of the two phase fluid through which the X ray beams transmit to the sum of the lengths of the steam bubbles through which the X ray beams transmit. Such a void ratio is specifically termed a local void ratio.

When the source of X rays 2, the X ray detector 3, the collimeter 5 and the slits 6 are moved in unison in a plane perpendicular to the axis of the cylindrical measuring unit 1, for example, toward the upper end as shown in FIG. 2, a void ratio $\alpha(x)$ for a height x of the X ray beams can be obtained in the same manner. An average void ratio $\bar{\alpha}$ in a cross-section can be obtained by integrating $\alpha(x)$ from a height of $x = -r_0$ to a height of $x = +r_0$ with a height $l_D = \sqrt{r_0^2 - x^2}$ added and then dividing the integrated value with the cross-sectional area $A = \pi r_0^2$ of the measuring unit 1. Thus, $$\bar{\alpha} = \left[ \int_{-r_0}^{+r_0} 2\sqrt{r_0^2 - x^2} \cdot \alpha(x) dx / \pi r_0^2 \right]$$

Then, it is possible to obtain an accurate cross-sectional average void ratio $\bar{\alpha}$. According to the prior art void ratio measuring apparatus, as shown in FIG. 3 a single fixed beam was used, or as shown in FIG. 4, three fixed X ray beams have been used. The source of radiation is difficult to handle. In a certain case, a source of $\gamma$ rays difficult to collimate has been used. With fixed three beams, error of the measurement of the cross-sectional average void ratio often amounts to more than 25% depending upon the mode of flow of the two phase fluid. For these reasons, the prior art apparatus of measuring void ratio with radiations are not suitable for practical use.

SUMMARY OF THE INVENTION

Accordingly, it is an object of this invention to provide an improved apparatus for measuring a void ratio by using radiations capable of accurately measuring a cross-sectional average void ratio $\alpha$ under a transient condition varying at a high speed.

Another object of this invention is to provide a novel apparatus for measuring a void ratio by using radiations which does not produce mechanical vibration and free from error caused by mechanical vibration.

According to this invention there is provided apparatus for measuring a void ratio by using radiations of the type comprising a hollow measuring unit through which fluid containing voids flows, a source of radiations and a radiation detector which are disposed on the opposite sides of the measuring unit, characterized in that there is provided a rotary disc disposed between the measuring unit and the radiation detector and provided with a plurality of measuring openings which are equally spaced around a periphery of the rotary disc for transmitting the radiations.

DESCRIPTION OF THE PREFERRED EMBODIMENT

Figure 1:
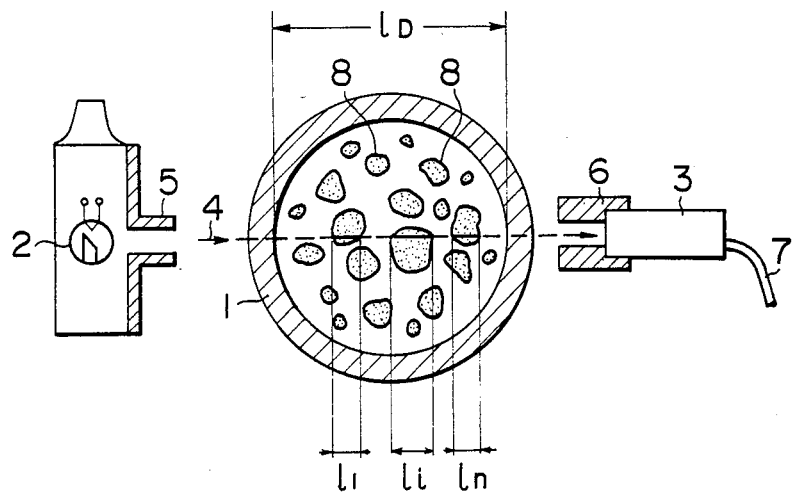
FIG. 1 is a diagrammatic cross-sectional view showing the principle of a prior art apparatus for measuring a void ratio by using X-rays.
Figure 2:
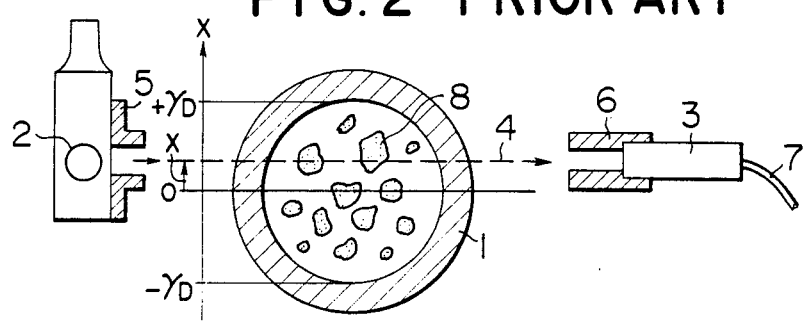
FIG. 2 is a dynamic cross-sectional view showing a prior art void ratio measuring apparatus showing the principle of measuring the local void ratio $\alpha(x)$ at a height x of an X ray beam.
Figure 3:
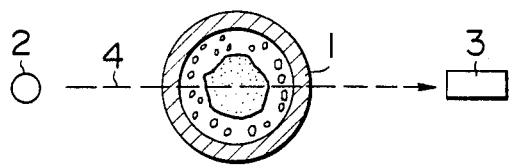
FIGS. 3 and 4 are diagrammatic cross-sectional views showing prior art void ratio measuring apparatus utilizing a single and three stationary X ray beams respectively.
Figure 4:
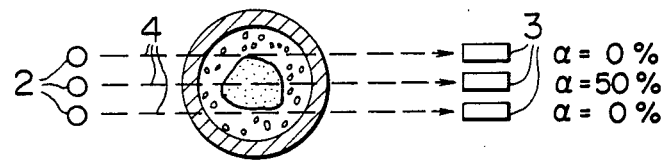
Figure 5:
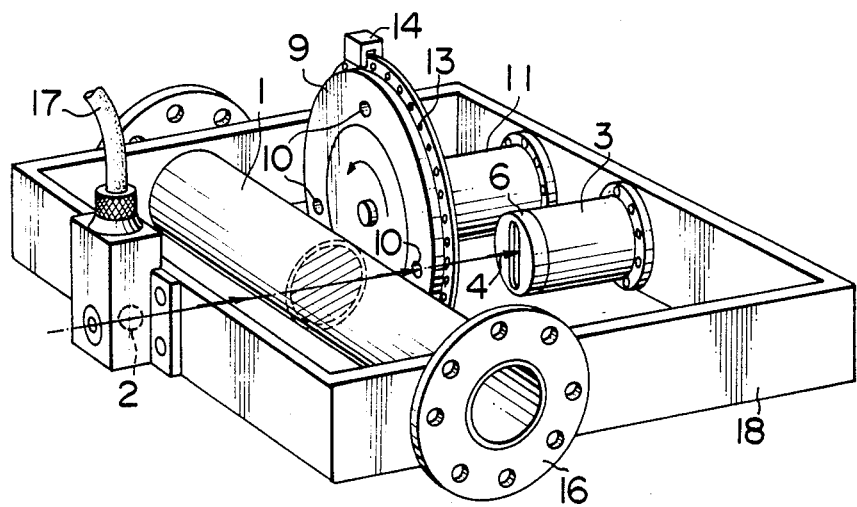
FIG. 5 is a perspective view showing one embodiment of this invention.

A preferred embodiment of this invention will be described hereunder with reference to FIG. 5 in which parts the same as or similar to those shown in FIG. 1 are designated by the same reference numerals. The void ratio measuring apparatus of this invention comprises a cylindrical measuring unit 1, a source of radiations 2 and a radiation detector 3 which are disposed on the opposite sides of the cylindrical measuring unit 1, and a rotary disc 9 disposed between the cylindrical measuring unit 1 and the radiation detector 3. The radiation utilized in this invention may be X rays, γ rays or other radiation that can transmit through the cylindrical measuring unit 1. The radiation detector 3 may be of any type so long as it can detect radiations transmitting through the measuring unit 1.

Figure 6:
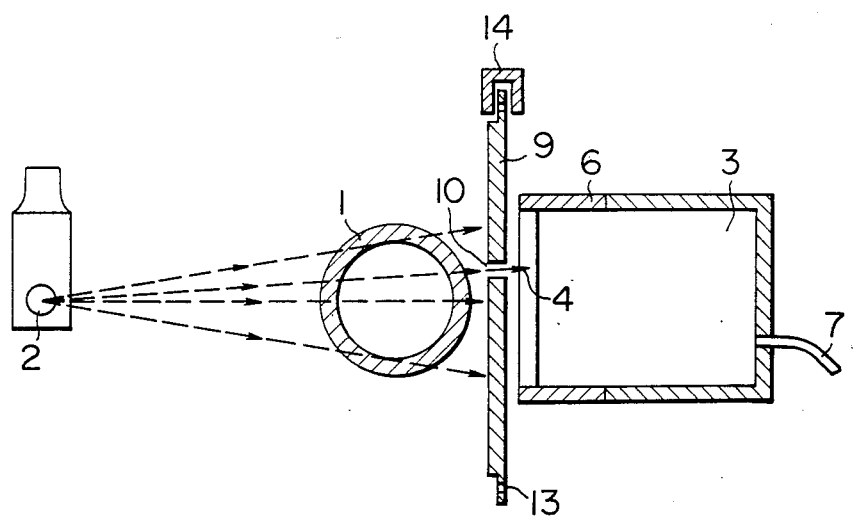
FIG. 6 is a diagrammatic sectional view useful to explain the principle of measuring of the apparatus shown in FIG. 5.
Figure 7:
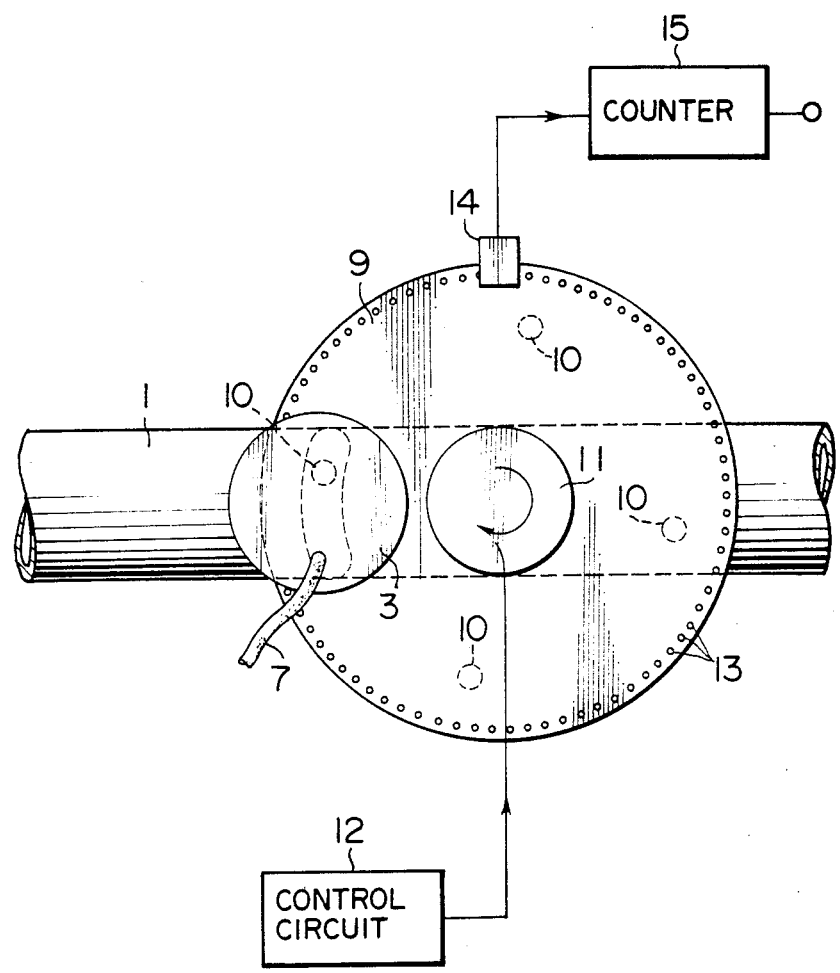
FIG. 7 is a diagramatic elevational view partly in section showing the construction of a rotary disc utilized in this invention and viewed from the side of a X ray detector.

The rotary disc 9 is provided with a plurality (in this example 4) of equally spaced small circular openings 10 disposed on the same circle so that only the radiation passed through the openings 10 forms fine radiation beams 4 reaching the radiation detector 3. When transmitting through the cylindrical measuring unit 1 the radiation beams 4 are attenuated according to the local void ratio of the two phase fluid in the measuring unit. As the rotary disc 9 is rotated the radiation beam 4 passing through each slit 10 scans the cylindrical measuring unit 1 from the lower portion to the upper portion thereof as shown in FIG. 6. The spacing between openings 10 is determined such that when the scanning of the measuring unit 1 by one opening is completed the scanning by another opening will be commenced. The rotary disc 9 is rotated by a directly coupled driving motor 11 which is controlled by a phase lock loop control circuit 12 to rotate at a constant speed. The thickness of the peripheral portion of the rotary disc 9 is decreased to form a flange as shown in FIG. 6, and a plurality of uniformly spaced small openings 13 are provided through the flange so as to convert light pulses passing through the openings 13 into electric signals by means of a photosensor 14. The number of the outputs of the photosensor 14 is counted by a counter 15 to measure the angle of rotation of the rotary disc 9. The counter is constructed such that its count is reset to zero at each 360° rotation. The cylindrical measuring unit 1 is made of metallic berylium. Since metallic berylium attenuates radiations in a lesser extent when the cylindrical measuring unit is made of metallic berylium, the state of the two phase fluid therein can be readily measured, thus improving the accuracy of measurement. Moreover, as the scanning time can be made shorter it is possible to accurately determine the cross-sectional average void ratio by determining a local void ratio distribution, even in high speed transient phenomena. Moreover, in the void ratio measuring apparatus according to this invention, since a rotary disc is used to scan the radiation beam, mechanical vibrations are small, thus enabling high speed scanning. In the present level of technology, the maximum scanning speed is limited by the response speed of the radiation detector 3. A NaI(Tl) scintillator integrally combined with a photoelectric multiplier is suitable for use as the radiation detector. From the standpoint of the theory of measurement, the scintillator should have an outer diameter larger than the inner diameter of the cylindrical measuring unit.

As above described the apparatus for measuring void ratios of this invention utilizing radiations can measure at high accuracies a local void ratio distribution of two phase fluid in a cylindrical measuring unit and a cross-sectional average void ratio even under high speed transient states. Moreover, use of a rotary disc decreases vibration, thereby enabling smooth scanning. It should be understood that the measuring unit is not limited to cylindrical form and that a polygonal cylinder or a box may be used.

I claim:

1. In apparatus for measuring a void ratio by using X-Ray radiation of the type comprising a hollow measuring unit through which fluid containing voids flows, a source of X-ray radiation and a radiation detector disposed on opposite sides of said measuring unit, the improvement which comprises an X-ray opaque rotary disc disposed between said measuring unit and said radiation detector and said disc having a first plurality of openings which are relatively small circular measuring openings substantially equal to the size of the voids to be detected and are equally spaced around a first circular path on said rotary disc for transmitting said radiation to said detector after passing through said hollow measuring unit, said measuring openings forming fine circular radiation beams, means for measuring the rotational angle of the disc comprising a second plurality of openings equally spaced around said disc on a second circular path which is radially spaced from said first circular path; means on one side of the disc for sending an optical signal through the second plurality of opening and an optical detector therefor on the other side of the disc and means connected to said optical detector for measuring the rotational angle of the disc and means for driving the disc at a constant speed.

2. The apparatus according to claim 1 in which said hollow measuring unit is made of metallic berylium.

* * * * *